United States Patent
Morita (10) Patent No.: US 12,023,115 B2
(45) Date of Patent: Jul. 2, 2024

(54) MEDICAL-ROBOT PNEUMATIC DRIVE MECHANISM

(71) Applicant: RIVERFIELD INC., Tokyo (JP)

(72) Inventor: Naoya Morita, Tokyo (JP)

(73) Assignee: RIVERFIELD INC., Tokyo (JP)

(*) Notice: Subject to any disclaimer, the term of this patent is extended or adjusted under 35 U.S.C. 154(b) by 13 days.

(21) Appl. No.: 17/896,684

(22) Filed: Aug. 26, 2022

(65) Prior Publication Data
US 2022/0412378 A1 Dec. 29, 2022

Related U.S. Application Data

(63) Continuation of application No. PCT/JP2020/016953, filed on Apr. 17, 2020.

(51) Int. Cl.
*F15B 15/14* (2006.01)
*A61B 34/30* (2016.01)
*F15B 7/00* (2006.01)

(52) U.S. Cl.
CPC .......... *A61B 34/30* (2016.02); *F15B 15/1404* (2013.01); *F15B 15/1409* (2013.01); *F15B 15/149* (2013.01); *F15B 7/001* (2013.01)

(58) Field of Classification Search
CPC  F15B 15/1404; F15B 15/1409; F15B 15/149; F15B 15/2815; F15B 15/2846
See application file for complete search history.

(56) References Cited

U.S. PATENT DOCUMENTS

| | | | | |
|---|---|---|---|---|
| 5,363,741 A * | 11/1994 | Takada | ................ | F16C 29/041 384/47 |
| 10,900,307 B2 * | 1/2021 | Al Hussin | ............... | E21B 23/04 |
| 11,725,675 B2 * | 8/2023 | Gückel | ................ | F15B 21/003 60/486 |
| 2013/0172812 A1 | 7/2013 | Kirschenman | | |
| 2022/0049725 A1 * | 2/2022 | Asaba | ................ | F15B 15/202 |
| 2022/0409312 A1 * | 12/2022 | Morita | ................ | A61B 34/30 |

FOREIGN PATENT DOCUMENTS

| | | |
|---|---|---|
| CN | 1295198 A | 5/2001 |
| CN | 103517684 A | 1/2014 |
| DE | 100 53 847 A1 | 5/2001 |
| EP | 0 603 459 A2 | 6/1994 |
| JP | 2001-132707 A | 5/2001 |
| JP | 2019-013445 A | 1/2019 |
| WO | 2016/051495 A1 | 4/2016 |
| WO | 2018/064400 A1 | 4/2018 |

OTHER PUBLICATIONS

European Search Report dated Mar. 28, 2023 in European Application No. 20931561.3.
Office Action dated Dec. 2, 2022 from the Chinese Patent Office in Application No. 202080095618.4.
International Search Report for PCT/JP2020/016953 dated Jul. 21, 2020.
Written Opinion for PCT/JP2020/016953 dated Jul. 21, 2020.

* cited by examiner

*Primary Examiner* — Michael Leslie
(74) *Attorney, Agent, or Firm* — Sughrue Mion, PLLC (57) ABSTRACT

A pneumatic drive for a medical robot includes a manifold having cylinders extending in a first direction, and respective rods corresponding to the cylinders, the rods extending on one side of the cylinders in the first direction. The manifold includes air supply ports that feed the cylinders with air for moving the respective rods forward and backward. The air supply ports are provided on another side of the manifold in the first direction.

14 Claims, 8 Drawing Sheets

MEDICAL-ROBOT PNEUMATIC DRIVE MECHANISM

CROSS REFERENCE TO RELATED APPLICATIONS

This U.S. Application is a continuation application of International Application No. PCT/JP2020/016953 filed Apr. 17, 2020, the contents of which being incorporated by reference herein in its entirety.

BACKGROUND

The present disclosure relates to a pneumatic drive for a medical robot that manipulates a surgical tool by an actuator.

In recent years, surgical operations using surgery assisting devices have come into widespread use. The surgery assisting device includes a surgical instrument that is inserted into the body cavity of a patient to perform various surgical operations. Because of the work environment of the surgical instruments, precise driving is required for patient safety.

SUMMARY

According to an aspect of one or more embodiments, there is provided a pneumatic drive for a medical robot comprising a manifold having a plurality of cylinders extending in a first direction; and respective rods corresponding to the plurality of cylinders, the rods extending on one side of the plurality of cylinders in the first direction, wherein the manifold has a plurality of air supply ports that feed the cylinders with air for moving the respective rods forward and backward, the plurality of air supply ports being provided on another side of the manifold in the first direction.

According to another aspect of one or more embodiments, there is provided a pneumatic drive for a medical robot, the pneumatic drive comprising a manifold comprising a plurality of cylinders extending in a first direction; and a plurality of rods corresponding respectively to the plurality of cylinders, the plurality of rods extending from one side of the plurality of cylinders in the first direction, wherein the manifold comprises a plurality of air supply ports that feed the plurality of cylinders with air for moving the plurality of rods forward and backward, the plurality of air supply ports being provided on another side of the manifold in the first direction.

According to yet another aspect of one or more embodiments, there is provided an apparatus for a medical robot, the apparatus comprising a manifold comprising a plurality of cylinders extending in a first direction; and a plurality of rods corresponding respectively to the plurality of cylinders, the plurality of rods extending from a first side of the manifold in the first direction, wherein the manifold comprises a plurality of first air ports corresponding respectively to the plurality of cylinders, the plurality of first air ports being provided on a second side of the manifold in the first direction, each first air port of the plurality of first air ports supplying air to a corresponding cylinder for a forward movement of the rod of the corresponding cylinder in a forward direction.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Surgery using medical robots is attracting attention as a technique that enhances the possibility of not only reducing the burden on a surgeon but also the burden on a patient through highly accurate and stable treatment as well as the possibility of remote medical care. In such medical robots, there is a medical robot in which a drive mechanism using pneumatic pressure is used as an actuator as the drive source for driving a surgical tool.

There is a manipulator system that can easily improve the accuracy of movement and suppress the occurrence of troubles due to disturbance in a surgical manipulator having a pneumatically driven external force detection function.

There is also a control system that executes pneumatic servo control for a pneumatically driven robot arm that holds and operates a medical device. The control system includes a switching unit and a control unit. The switching unit switches between a passive operation mode and an active operation mode. In the active operation mode, the control unit sets a target pressure based on a result of positional control using an error of the current position of a robot arm with respect to a target position and executes the pressure control based on the target pressure. In the passive operation mode, the control unit sets a target pressure required for self-weight compensation from the current position of the robot arm and executes the pressure control based on the target pressure.

When a drive mechanism using pneumatic pressure is used as the drive source for driving a surgical tool in a medical robot, it is advantageous to reduce the size of the drive mechanism. In particular, as the control of the operation, orientation, angle, etc. of the surgical tool is complicated, a number of drive sources are required to independently drive each operation. The size of the drive mechanism increases as the number of drive sources increases, so a technique to reduce the size of the drive mechanism is important.

An aspect of various embodiments is to provide a pneumatic drive for a medical robot that is capable of reducing the size of the device configuration.

According to an aspect of one or more embodiments, there is provided a pneumatic drive for a medical robot. The pneumatic drive may include a manifold having a plurality of cylinders extending in a first direction; and respective rods corresponding to the plurality of cylinders. The rods extend on one side in the first direction. The manifold further has a plurality of air supply ports that feed the cylinders with air for moving the respective rods forward and backward. The air supply ports are provided on the other side in the first direction in the manifold.

According to such a configuration, all of the plurality of air supply ports that feed the cylinders with air for moving the rods forward and backward are provided on the other side in the first direction in the manifold, and it is therefore possible to consolidate the arrangement of the plurality of air supply ports on one side (rear side) of the manifold to reduce the size of the device configuration.

In the pneumatic drive for a medical robot, the plurality of cylinders may be arranged in a second direction orthogonal to the first direction. This configuration allows the plurality of air supply ports to be consolidated in a direction different from the direction (second direction) in which the plurality of cylinders is arranged in the manifold.

In the pneumatic drive for a medical robot, a pipe located between one of the plurality of air supply ports and the one side of the cylinder may be provided to supply air for backward movement of the rod to the one side of the cylinder, and the pipe may be juxtaposed with the cylinder and extends in the first direction. With this configuration, the pipe communicating with one of the plurality of air supply ports consolidated on the other side of the manifold can be extended in the first direction to send air to the one side of the cylinder.

In the pneumatic drive for a medical robot, a plurality of pipes may be provided corresponding to the plurality of respective cylinders, and the plurality of pipes may be provided so as to be arranged in the second direction orthogonal to the first direction. With this configuration, the plurality of cylinders and the plurality of pipes are arranged in the second direction thereby to achieve an efficient layout of the cylinders and the pipes.

The pneumatic drive for a medical robot may include a peripheral member attached using the manifold as a reference. The manifold itself can be used as a structural member by making the plurality of cylinders into a manifold, and the peripheral member can therefore be disposed on the manifold as a reference.

In the pneumatic drive for a medical robot, a linear encoder may be provided corresponding to each of the plurality of cylinders, and the peripheral member may include a detector of the linear encoder. This configuration allows the detector of the linear encoder to be disposed at a position that does not interfere with the air supply ports. Moreover, the relative position between the detector and a linear motion guide supporting a scale portion of the linear encoder can be set with the same accuracy as the positioning accuracy between the linear motion guide and the manifold.

In the pneumatic drive for a medical robot, a substrate on which the plurality of the detectors is mounted may be provided as the peripheral member, and the substrate may be provided on the manifold so that the plurality of detectors is juxtaposed in the second direction orthogonal to the first direction. This configuration allows the substrate to be provided on the manifold, and the plurality of detectors can thereby be arranged to line up with the plurality of cylinders.

According to various embodiments, it is possible to provide a pneumatic drive for a medical robot capable of reducing the size of the device configuration.

Hereinafter, one or more embodiments will be described with reference to the drawings. In the following description, the same members are denoted by the same reference numerals and the description of members once explained may be omitted.

(Configuration of Pneumatic Drive)

Figure 1:
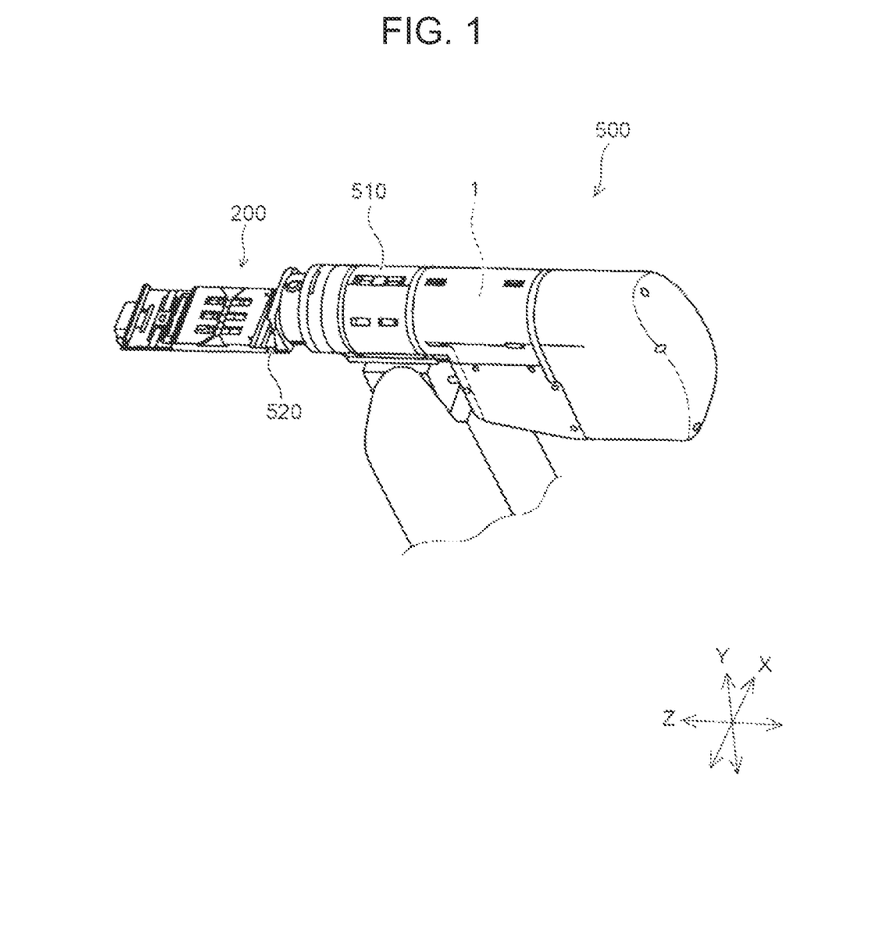
FIG. 1 is a perspective view exemplifying a medical robot, according to some embodiments.

FIG. 1 is a perspective view exemplifying a medical robot, according to some embodiments.

Figure 2:
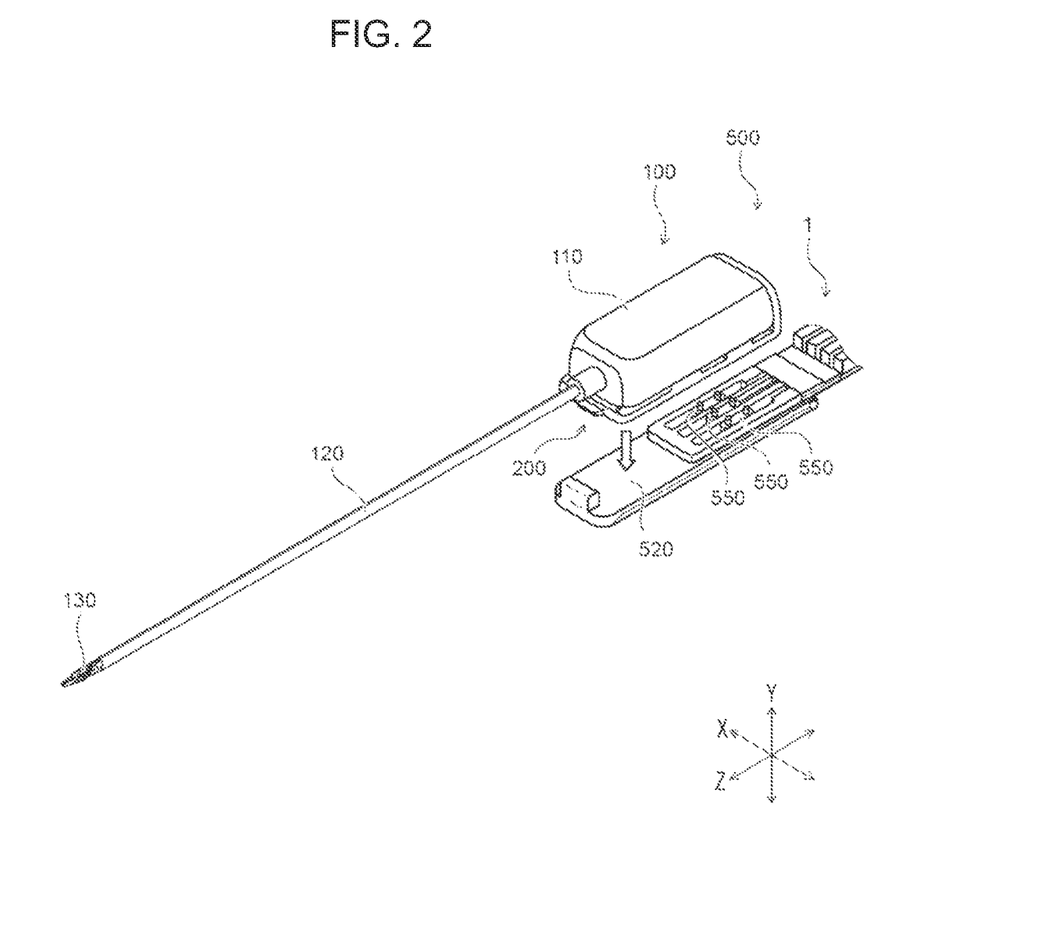
FIG. 2 is a perspective view exemplifying the attaching state of a surgical tool according to some embodiments.

FIG. 2 is a perspective view exemplifying the attaching state of a surgical tool, according to some embodiments.

Figure 3:
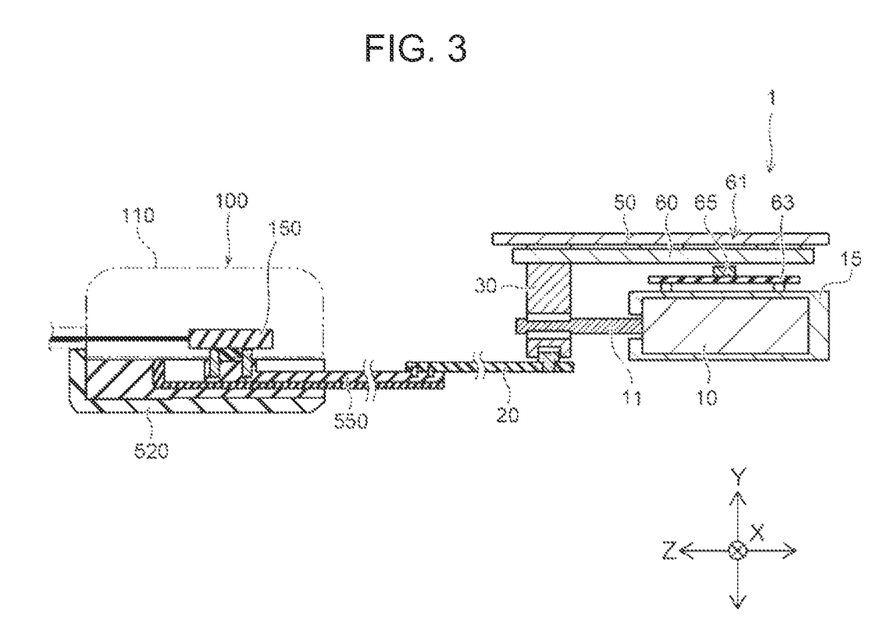
FIG. 3 is a schematic cross-sectional view exemplifying a pneumatic drive for a medical robot according to some embodiments.

FIG. 3 is a schematic cross-sectional view exemplifying a pneumatic drive for a medical robot according to some embodiments.

As illustrated in FIGS. 1 and 2, a medical robot 500 has a multi-degree-of-freedom arm 510 that is a manipulator may be remotely controlled. The tip portion of the multi-degree-of-freedom arm 510 is provided with a mounting portion 520 to which a surgical tool 100 is attached. The surgical tool 100 is attached to the multi-degree-of-freedom arm 510 via a drape 200.

The drape 200 is disposed between the medical robot 500, which holds the surgical tool 100, and the surgical tool 100 and serves to isolate the surgical tool 100 and the medical robot 500 from each other. The drape 200 also serves to transmit power in the forward/backward direction from power transmission parts 550 of the medical robot 500 to movable parts 150 (see FIG. 3) provided in the surgical tool 100.

The tip portion (mounting portion 520) of the multi-degree-of-freedom arm 510 is configured to be rotatable around an axis in the extending direction. The arm portion of the multi-degree-of-freedom arm 510 is also axially rotatable. The surgical tool 100 attached to the medical robot 500 can therefore approach a patient from various angles by using the multi-degree-of-freedom arm 510.

As illustrated in FIG. 2, is an exemplary embodiment of the surgical tool 100 includes a main body 110, a shaft 120 extending from the main body 110, and a treatment part 130 provided at the tip of the shaft 120 (an end portion opposite to the main body 110). The treatment part 130 is, for example, forceps.

The medical robot 500 is provided with a pneumatic drive 1 for driving the power transmission parts 550. The pneumatic drive 1 is incorporated in the housing of the multi-degree-of-freedom arm 510 (see FIG. 1).

As illustrated in FIG. 3, the pneumatic drive 1 may include: a manifold 15 that has cylinders 10; and rods 11 that move forward and backward in a direction in which the cylinders 10 extend. Here, in the present embodiment, the direction in which the cylinders 10 extend (forward/backward movement direction of the rods 11) will be referred to as a Z direction, one of the directions orthogonal to the Z direction will be referred to as an X direction, and the direction orthogonal to the Z direction and the X direction will be referred to as a Y direction. The Z direction is an example of the first direction, and any of the X direction and Y direction orthogonal to the Z direction is an example of the second direction.

Between the pneumatic drive 1 and the surgical tool 100, operation members 20 operated by the driving force of the pneumatic drive 1 and transmission members 30 located between the pneumatic drive 1 and the operation members 20 are provided.

The pneumatic drive 1 sends air to the cylinders 10 based on control signals output from a control unit (not illustrated) and linearly moves the rods 11 in the forward/backward direction (Z direction) by the balance of pneumatic pressures in the cylinders 10. The forward/backward operations of the rods 11 are transmitted from the transmission members 30 to the operation members 20, drive the power transmission parts 550, and are transmitted to the surgical tool 100. The driving force transmitted to the surgical tool 100 is transmitted from the power transmission parts 550 to the movable parts 150, and the treatment part 130 is operated by the operations of the movable parts 150.

(Specific Example of Pneumatic Drive)

Figure 4:
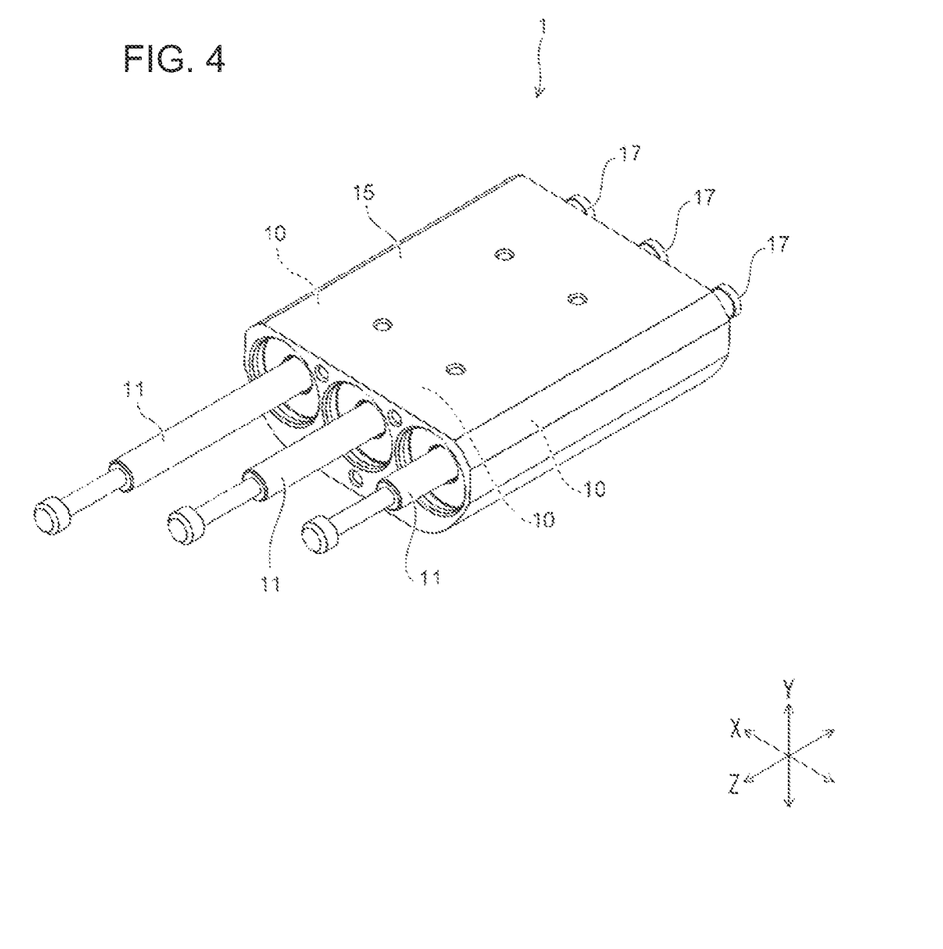
FIG. 4 is a perspective view exemplifying the pneumatic drive according to some embodiments.
Figure 5:
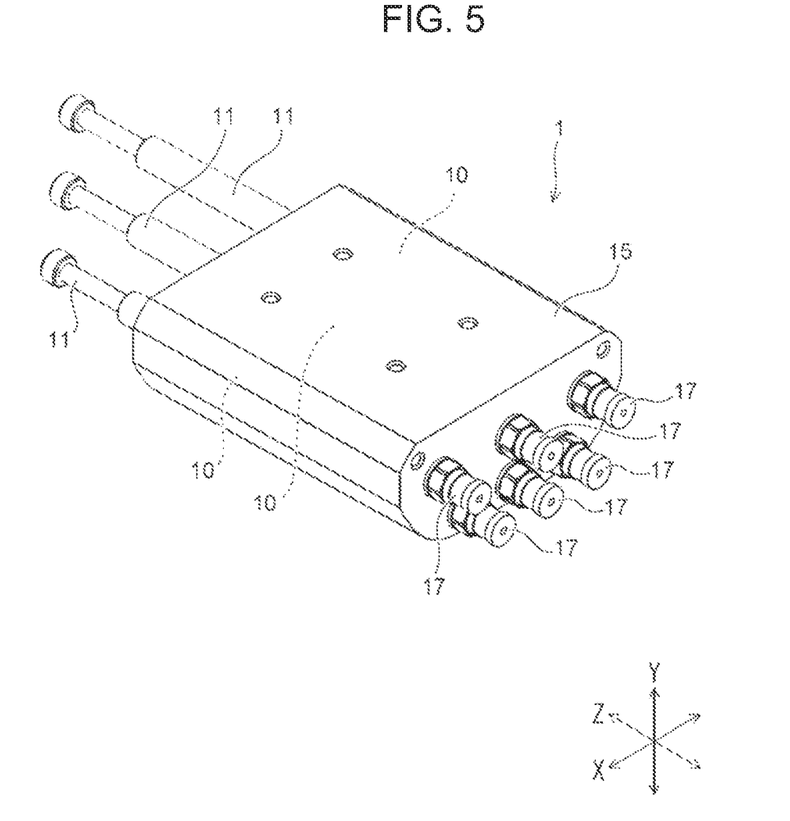
FIG. 5 is a perspective view exemplifying the pneumatic drive according to some embodiments.

FIGS. 4 and 5 are perspective views exemplifying the pneumatic drive according to some embodiments. FIG. 4 illustrates a perspective view of the pneumatic drive 1 as seen from the rods 11 side, and FIG. 5 illustrates a perspective view of the pneumatic drive 1 as seen from the side opposite to the rods 11. For descriptive purposes, the side on which the rods 11 extend in the Z direction will be referred to as one side, and the side opposite to the side on which the rods 11 extend in the Z direction will be referred to as the other side.

In the pneumatic drive 1 according to some embodiments, the manifold 15 is provided with a plurality of cylinders 10. The cylinders 10 extend in the Z direction and are juxtaposed with each other in the X direction. That is, the plurality of cylinders 10 is arranged in the Z direction. In the example illustrated in FIGS. 4 and 5, three cylinders 10 are juxtaposed with each other in the X direction and are arranged parallel to the Z direction. The three cylinders 10 are provided with respective rods 11 that can move forward and backward in the Z direction. The operations of the rods 11 of the three cylinders 10 are independent, and the position (forward/backward operation) of each rod 11 in the Z direction is individually controlled by the air fed to the corresponding cylinder 10.

The manifold 15 is provided with air supply ports 17 for feeding respective cylinders 10 with air. The air supply ports 17 are used as ports for supplying air into the cylinders 10, and as ports for discharging air to the outside of the cylinders 10. For descriptive purposes, these ports will be described by referring to them as the air supply ports 17.

At least two air supply ports 17 are provided for moving a rod 11 forward and backward with respect to one cylinder 10. In the present embodiment, two air supply ports 17 correspond to one cylinder 10, and a total of six air supply ports 17 are therefore provided for the three cylinders 10. All of these six air supply ports 17 are provided on the other side of the manifold 15 in the Z direction (the side opposite to the rods 11).

Thus, making the plurality of cylinders 10 into a manifold contributes to a reduced size of the device. That is, the rigidity of the plurality of cylinders 10 alone is not high, and it is difficult to use the cylinders 10 as structural members. If the cylinders 10 are used as structural members, the size is increased in order to increase the rigidity. In the present embodiment, the rigidity of the manifold 15 is increased by making the plurality of cylinders 10 into a manifold, and the manifold 15 itself can be used as a structural member. Moreover, the manifold 15 can be used as a reference for attaching peripheral members by utilizing the rigidity of the manifold 15. These can contribute to a reduced size of the device. Furthermore, all of the plurality of air supply ports 17 are provided on the other side of the manifold 15, and the arrangement of the plurality of air supply ports 17 can thereby be consolidated on the one side (rear side) of the manifold 15 to reduce the size of the device configuration. In some embodiments, even in the pneumatic drive 1 including the plurality of cylinders 10 and the plurality of air supply ports 17 which supply air to the cylinders 10 in one manifold, the efficient layout achieves a reduced size of the device through juxtaposing the plurality of cylinders 10 in the X direction in the manifold 15 and consolidating all the air supply ports 17 on the other side in the Z direction.

(Operation of Pneumatic Drive)

Figure 6A:
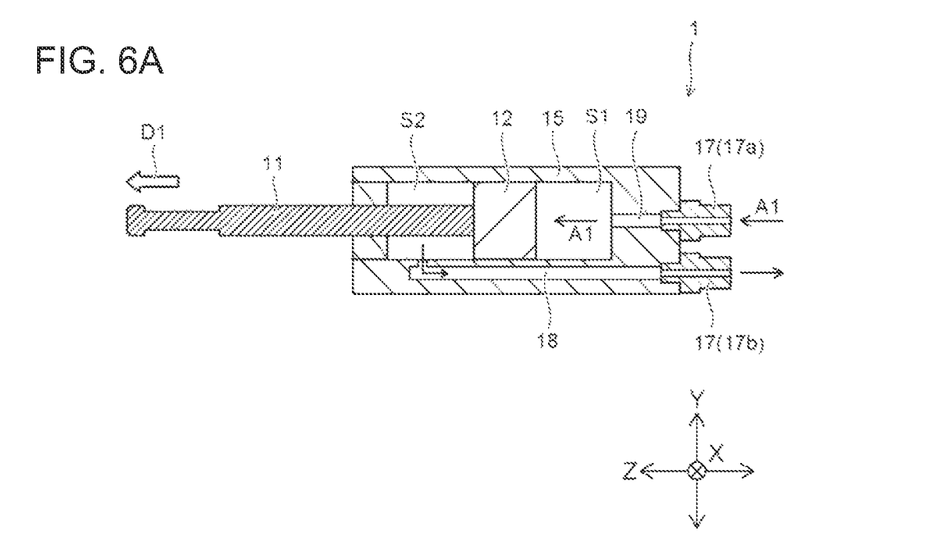
FIGS. 6A and 6B are schematic cross-sectional views exemplifying the operation of the pneumatic drive according to some embodiments.
Figure 6B:
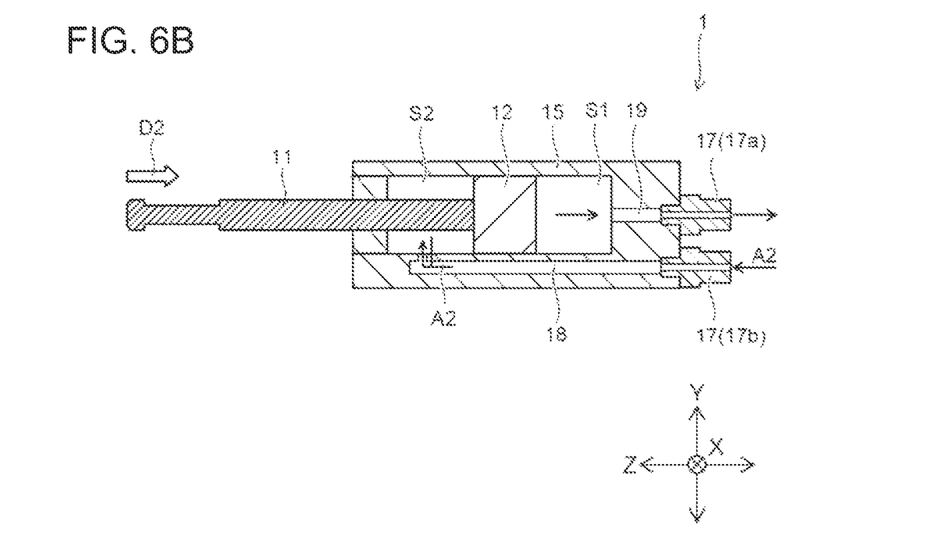

FIGS. 6A and 6B are schematic cross-sectional views exemplifying the operation of the pneumatic drive according to some embodiments. The manifold 15 of the pneumatic drive 1 is provided with a pipe 18 that communicates with one of the air supply ports 17. The pipe 18 is located between one of the air supply ports 17 and the one side of a cylinder 10 and is provided to supply air for backward movement of the rod to the one side of the cylinder 10. The pipe 18 is provided in the manifold 15 so as to be juxtaposed with the cylinder 10 and extend in the Z direction. Even though the air supply ports 17 are consolidated on the other side of the manifold 15, the pipe 18 can send air from that air supply port 17 to the one side of the cylinder 10.

Although not illustrated in FIGS. 6A and 6B, in some embodiments the pipe 18 is provided corresponding to each of the plurality of cylinders 10. Each of the pipes 18 extends in the Z direction along the corresponding cylinder 10, and the pipes 18 are provided in the manifold 15 so as to be juxtaposed with each other in the X direction. In some embodiments, the pipes 18 may be provided on the one side of the manifold 15 in the Y direction (one side in the Y direction with respect to the cylinders 10). This configuration allows all of the plurality of pipes 18 to be consolidated on the one side of the cylinders 10 in the Y direction, and the length (thickness) of the manifold 15 in the Y direction can be suppressed as compared with a case in which the pipes 18 are provided on both sides of the cylinders 10 in the Y direction.

Here, in the two air supply ports 17 provided for one cylinder 10, the port which supplies the air for moving the rod 11 forward (air for forward movement A1) will be referred to as an air supply port 17a, and the port which supplies the air for moving the rod 11 backward (air for backward movement A2) will be referred to as an air supply port 17b.

The cylinder 10 is provided with a piston 12, and the rod 11 is operated to move forward and backward by the piston 12 which moves in the cylinder 10. The other side of the cylinder 10 is provided with a communication hole 19 that communicates with a space S1 on the other side of the piston 12 in the cylinder 10. The communication hole 19 is provided from the space S1 to the other end of the cylinder 10 in the Z direction. The communication hole 19 may be provided on the extension of the rod 11 in the Z direction (on the extension of the central axis of the cylinder 10). The communication hole 19 is provided with the air supply port 17a.

The pipe 18 communicates with a space S2 on the one side of the piston 12 in the cylinder 10, extends in the Z direction in parallel with the cylinder 10, and is provided up to the other end of the cylinder 10. The pipe 18 is provided with the air supply port 17b. This configuration allows the air supply ports 17a and 17b to be consolidated and juxtaposed on the other side of the cylinder 10.

As illustrated in FIG. 6A, when the air for forward movement A1 is supplied to the space S1 from the air supply port 17a, the pneumatic pressure in the space S1 becomes higher than that in the space S2, and the piston 12 is moved to the one side in the Z direction. This operation allows the rod 11 to operate to move forward (see arrow D1). During this operation, the air in the space S2 may be discharged from the air supply port 17b to the outside of the piston 12 through the pipe 18, or may be sucked from the air supply port 17b.

On the other hand, as illustrated in FIG. 6B, when the air for backward movement A2 is supplied to the space S2 from the air supply port 17b, the pneumatic pressure in the space S2 becomes higher than that in the space S1, and the piston 12 is moved to the other side in the Z direction. This operation allows the rod 11 to operate to move backward (see arrow D2). During this operation, the air in the space S1 may be discharged from the air supply port 17a to the outside of the piston 12 through the communication hole 19, or may be sucked from the air supply port 17a.

As in the pneumatic drive 1 according to some embodiments, when the pipes 18 arranged in the X direction are provided corresponding to respective cylinders 10, the cylinders 10 and the pipes 18 are arranged in the X direction, and an efficient layout of the cylinders 10 and pipes 18 is realized. Moreover, all the air supply ports 17 are consolidated on the other side of the manifold 15; therefore, there is no member of the manifold 15 protruding in the X direction or the Y direction, and a reduced size of the device can be achieved. This configuration can enhance the degree of freedom in design when incorporating the pneumatic drive 1 into the multi-degree-of-freedom arm 510 of the medical robot 500 and easily achieve a reduced size of the entire medical robot 500.

(Configuration with Linear Encoder)

The configuration with a linear encoder in the pneumatic drive 1 according to some embodiments will then be described.

Figure 7A:
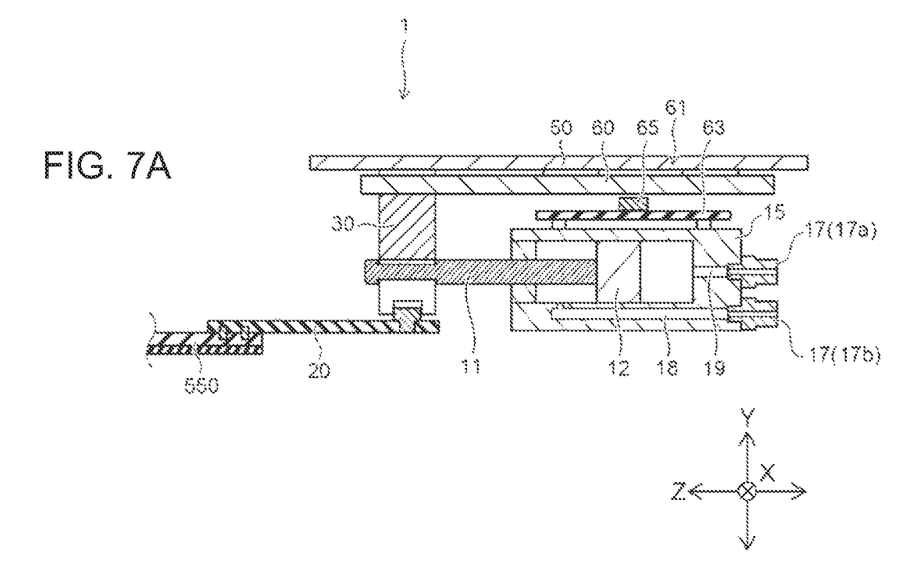
FIGS. 7A and 7B are schematic cross-sectional views exemplifying a pneumatic drive provided with a linear encoder according to some embodiments.
Figure 7B:
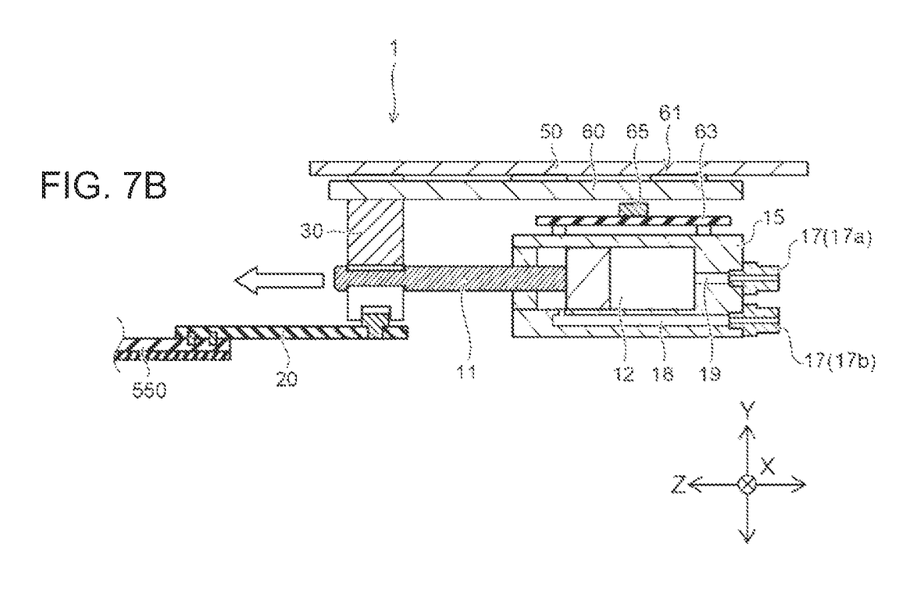

FIGS. 7A and 7B are schematic cross-sectional views exemplifying a pneumatic drive provided with a linear encoder, according to some embodiments.

One end portion in the Y direction of the transmission member 30 provided between the rod 11 and the operation member 20 is fixed to a scale portion 60 of a linear encoder 61 supported by a linear motion guide 50. The linear motion guide 50 supports the scale portion 60 so that it is movable in the Z direction. The transmission member 30 therefore comes to a state of being supported by the linear motion guide 50 via the scale portion 60 and is supported so as to be linearly movable in the Z direction together with the scale portion 60.

When the rod 11 is driven in the Z direction by the pneumatic drive 1 from the state illustrated in FIG. 7A to the state illustrated in FIG. 7B, the scale portion 60 moves in the Z direction along the linear motion guide 50 via the transmission member 30 as the rod 11 moves in the Z direction. A substrate 63 on which a detector 65 of the linear encoder 61 is mounted is attached to the manifold 15 facing the scale portion 60. The substrate 63 on which the detector 65 is mounted is a peripheral member provided on the manifold 15 by using the manifold 15 as a reference for attaching the peripheral member. This configuration allows the scale portion 60 and the detector 65 to be arranged so as to face each other. In some embodiments for the linear encoder 61 operate, the relative position between the linear motion guide 50, which supports the scale portion 60 as a movable component, and the detectors 65 may be set accurate. It is easy to accurately position the manifold 15 with respect to the linear motion guide 50 because the manifold 15 is a structural member. Accordingly, the relative position between the linear motion guide 50 and the detector 65 can be set with the same accuracy as the positioning accuracy between the linear motion guide 50 and the manifold 15. Moreover, the scale portion 60 is movable and the detector 65 is fixed; therefore, the wiring of the detector 65 is also fixed and can be easily routed, and the durability of the wiring can thus be improved.

Furthermore, the rigidity of the scale portion 60, which is a large member, suppresses the movement of the transmission member 30 in the X direction and the Y direction. This configuration allows the transmission member 30 to accurately move in the Z direction. In some embodiments, the accuracy of the linear motion of the manipulation member 20 is ensured by the linear motion guide 50 which supports the scale portion 60. It therefore suffices that the pneumatic drive 1 is capable of driving, and the driving direction of the rod 11 may be slightly deviated.

Figure 8:
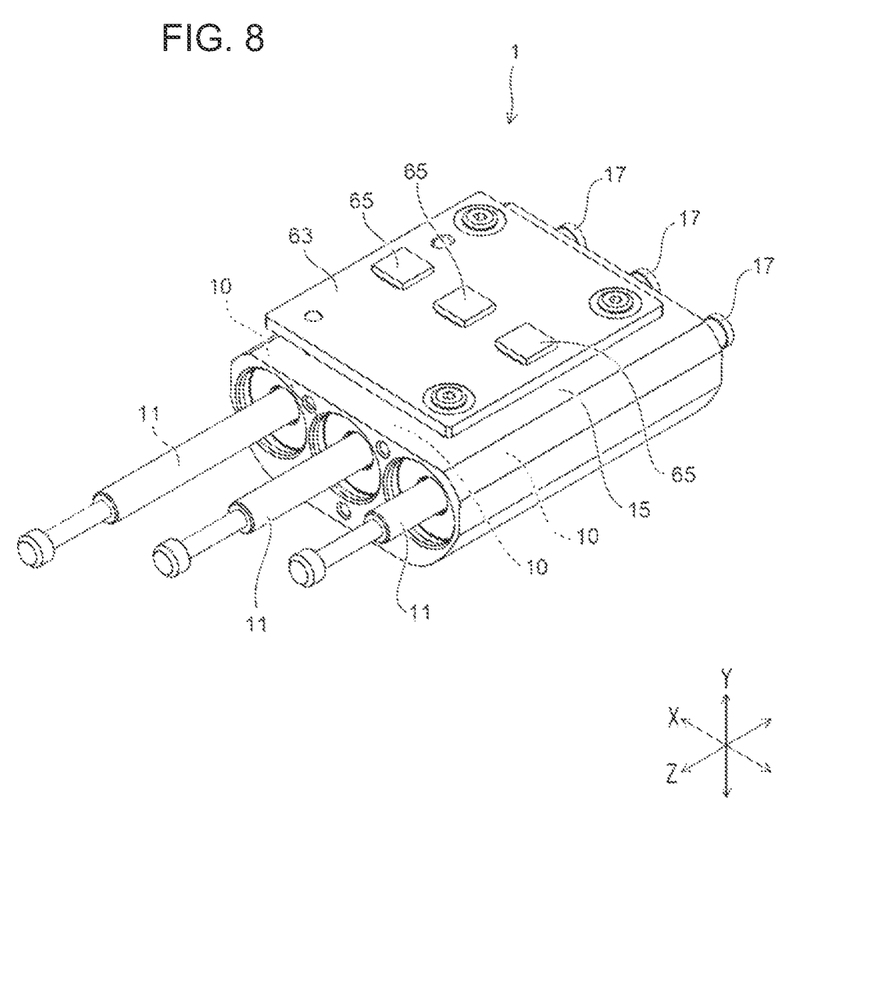
FIG. 8 is a perspective view exemplifying the layout of detectors provided on a manifold having a plurality of cylinders according to some embodiments.

FIG. 8 is a perspective view exemplifying the layout of detectors provided on a manifold having a plurality of cylinders, according to some embodiments.

In the manifold 15 having a plurality of cylinders 10, the cylinders 10 are provided with respective scale portions 60. The detectors 65 facing the respective scale portions 60 are mounted on the substrate 63 and are provided on the manifold 15 via the substrate 63.

The substrate 63 is attached onto the manifold 15 so that the detectors 65 are juxtaposed with each other in the X direction. With this configuration, by providing the substrate 63 on the manifold 15, the detectors 65 can be arranged so as to be aligned with the cylinders 10.

In some embodiments, the air supply ports 17 are consolidated on the other side of the manifold 15; therefore, there is a sufficient area (positions that do not interfere with the air supply ports 17) for attaching the substrate 63 onto the manifold 15, and the detectors 65 can be easily arranged to face the respective scale portions 60 via one substrate 63 in a state of being juxtaposed in the X direction.

Thus, according to some embodiments, the pneumatic drive 1 for the medical robot 500 can be reduced in size even with a device configuration having a plurality of cylinders 10.

Although various embodiments have been described above, the present disclosure is not limited to these examples. For example, an example has been described in which one manifold 15 includes three cylinders 10 and three rods 11, but the number is not limited to three. Moreover, an example of the forceps has been described as the treatment part 130 of the surgical tool 100, but a treatment part 130 other than the forceps may be employed. Although the substrate 63 on which the detector 65 is mounted has been described as a specific example of the peripheral member, the detector 65 may be provided directly on the manifold 15. In this case, the detector 65 is a peripheral member by itself. Furthermore, the scope of the present disclosure encompasses those to which a person skilled in the art appropriately makes addition or removal of constitutional elements or design changes with respect to the previously-described embodiments or specific examples and those in which features of the embodiments are appropriately combined, provided that they have the subject matters of the present disclosure.

It should be understood that the present disclosure is not limited to the above embodiments, but various other changes and modifications may be made therein without departing from the spirit and scope of the appended claims.

What is claimed is:

1. A pneumatic drive for a medical robot, the pneumatic drive comprising:
   a manifold having a plurality of cylinders extending in a first direction; and
   respective rods corresponding to the plurality of cylinders, the rods extending on one side of the plurality of cylinders in the first direction, wherein the manifold has a plurality of air supply ports that feed the cylinders with air for moving the respective rods forward and backward, the plurality of air supply ports being provided on another side of the manifold in the first direction, wherein a pipe located between one of the plurality of air supply ports and the one side of the cylinder is provided to supply air for backward movement of the rod to the one side of the cylinder, and wherein the pipe is juxtaposed with the cylinder and extends in the first direction.

2. The pneumatic drive for a medical robot according to claim 1, wherein the plurality of cylinders is arranged in a second direction orthogonal to the first direction.

3. The pneumatic drive for a medical robot according to claim 1, wherein a plurality of the pipes is provided corresponding to the plurality of respective cylinders, and the plurality of the pipes is provided so as to be arranged in the second direction orthogonal to the first direction.

4. The pneumatic drive for a medical robot according to claim 1, further comprising a peripheral member that is attached on the manifold using the manifold as a reference.

5. The pneumatic drive for a medical robot according to claim 4, wherein a linear encoder is provided corresponding to each of the plurality of cylinders, and the peripheral member includes a detector of the linear encoder.

6. The pneumatic drive for a medical robot according to claim 5, wherein:

a substrate on which the plurality of the detectors is mounted is provided as the peripheral member, and the substrate is provided on the manifold so that the plurality of detectors is juxtaposed in a second direction orthogonal to the first direction.

7. A pneumatic drive for a medical robot, the pneumatic drive comprising:

a manifold comprising a plurality of cylinders extending in a first direction; and a plurality of rods corresponding respectively to the plurality of cylinders, the plurality of rods extending from one side of the plurality of cylinders in the first direction, wherein the manifold comprises a plurality of air supply ports that feed the plurality of cylinders with air for moving the plurality of rods forward and backward, the plurality of air supply ports being provided on another side of the manifold in the first direction, wherein a pipe provided between one of the plurality of air supply ports and the one side of a corresponding cylinder to supply air for a backward movement of the rod of the corresponding cylinder, and wherein the pipe is juxtaposed with the corresponding cylinder and extends in the first direction.

8. The pneumatic drive for a medical robot according to claim 7, wherein the plurality of cylinders is arranged in a second direction orthogonal to the first direction.

9. The pneumatic drive for a medical robot according to claim 7, further comprising a plurality of pipes corresponding respectively to the plurality of cylinders, and the plurality of the pipes is arranged in a second direction orthogonal to the first direction.

10. The pneumatic drive for a medical robot according to claim 7, further comprising a peripheral member that is attached on the manifold using the manifold as a reference.

11. The pneumatic drive for a medical robot according to claim 10, further comprising a plurality of linear encoders corresponding respectively to the plurality of cylinders, and each of the plurality of linear encoders comprises a detector.

12. The pneumatic drive for a medical robot according to claim 11, wherein the peripheral member comprises a substrate, and the plurality of detectors are mounted on the substrate, and the substrate is provided on the manifold so that the plurality of detectors is juxtaposed in a second direction orthogonal to the first direction.

13. An apparatus for a medical robot, the apparatus comprising:

a manifold comprising a plurality of cylinders extending in a first direction; and a plurality of rods corresponding respectively to the plurality of cylinders, the plurality of rods extending from a first side of the manifold in the first direction, wherein the manifold comprises:

a plurality of first air ports corresponding respectively to the plurality of cylinders, the plurality of first air ports being provided on a second side of the manifold in the first direction, each first air port of the plurality of first air ports supplying air to a corresponding cylinder for a forward movement of the rod of the corresponding cylinder in a forward direction, a plurality of pipes corresponding respectively to the plurality of cylinders, and a plurality of second air ports provided on the second side of the manifold in the first direction, wherein each pipe of the plurality of pipes is communicatively connected between a corresponding cylinder of the plurality of cylinders at a side of the corresponding cylinder from which the rod of the corresponding cylinder extends and a corresponding second air port of the plurality of second air ports, the corresponding second air port supplying air for a backward movement of the rod of the corresponding cylinder.

14. The apparatus of claim 13, wherein the plurality of cylinders have a width in a second direction orthogonal to the first direction.

* * * * *